(12) United States Patent
Ueno

(10) Patent No.: US 9,292,637 B2
(45) Date of Patent: Mar. 22, 2016

(54) METHOD FOR SIMULATING POLYMER MATERIAL

(71) Applicant: SUMITOMO RUBBER INDUSTRIES, LTD., Kobe-shi, Hyogo (JP)

(72) Inventor: Shinichi Ueno, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 458 days.

(21) Appl. No.: 13/914,977

(22) Filed: Jun. 11, 2013

(65) Prior Publication Data
US 2014/0012554 A1    Jan. 9, 2014

(30) Foreign Application Priority Data

Jul. 5, 2012 (JP) .................................. 2012-151705

(51) Int. Cl.
G06G 7/48 (2006.01)
G06F 17/50 (2006.01)
G06F 19/00 (2011.01)

(52) U.S. Cl.
CPC .......... *G06F 17/5018* (2013.01); *G06F 19/704* (2013.01)

(58) Field of Classification Search
None
See application file for complete search history.

(56) References Cited

FOREIGN PATENT DOCUMENTS

JP    2006-64658 A    3/2006

OTHER PUBLICATIONS

Rao et al. Computational Experiments on Filled Rubber Viscoelasticity: What is the Role of Particle—Particle Interaction? Macromolecules 2006, 39, pp. 6744-6751.*
Elliot et al. A Dissipative Particle Dynamics Method for Modeling the Geometrical Packing of Filler Particles in Polymer Composites Journal of Chemical Physics, vol. 113, No. 22, Dec. 2000.*
Katsumi Hagita Coarse-Grained Molecular Dynamics Simulation Approach for Polymer Nano-Composites Rubber ISSP.U.Tokyo.AC. JP 2009.*

\* cited by examiner

*Primary Examiner* — Omar Fernandez Rivas
*Assistant Examiner* — Cuong Luu
(74) *Attorney, Agent, or Firm* — Birch, Stewart, Kolasch & Birch, LLP

(57) ABSTRACT

A computer-implemented method for simulating a polymer material comprising a polymer, a filler and a modifying agent for increasing the affinity of the polymer to the filler is disclosed. A pair of filler models are defined by a pair of parallelly-opposed wall surfaces of a virtual space in which the modified polymer models are disposed, and a molecular dynamics calculation is performed. In order to evaluate the affinity, the number of the particles of the modified polymer models 2 moved into and staying in a nearby-filler area is counted at constant time steps, and the variation of the counted numbers is smoothened by averaging every two or more successive counted numbers.

4 Claims, 11 Drawing Sheets

METHOD FOR SIMULATING POLYMER MATERIAL

BACKGROUND OF THE INVENTION

The present invention relates to a computer-implemented method for simulating a polymer material including a polymer, a filler and a modifying agent for increasing the affinity of the polymer to the filler, and evaluating the affinity, more particularly to a combination of a modified polymer model and a filler model which is specifically defined by a flat surface fixed to a space in which the modified polymer model is disposed.

In general, a rubber compound used in a pneumatic tire contains reinforcing filler such as carbon black and silica. For example, if a silica-rich compound is used as a tread rubber of a pneumatic tire, an internal energy loss of the tread rubber is decreased and the tire performance, e.g. rolling resistance may be improved. Such silica-rich compound contains a modifying agent to increase the affinity of the base rubber or elastomer to the silica filler. If the affinity is low, the strength of the rubber compound is decreased with the increase in the content of the filler.

In recent years, on the other hand, in order to develop a rubber compound, the use of a computer simulation is proposed.

Japanese Patent Application Publication No. 2006-064658 discloses a computer-implemented method for evaluating a rubber material containing rubber and carbon black, and teaches to use a carbon model defined according to the molecular structure of the carbon black namely a graphite structure containing carbon atoms and a rubber model defined according to the molecular structure of the base rubber.

If such carbon models and rubber models are arranged dispersively, freely-movably in a virtual space, and a relaxation calculation is made based on molecular dynamics, then it takes much time to complete the relaxation calculation.

SUMMARY OF THE INVENTION

It is therefore, an object of the present invention to provide a computer-implemented method for simulating a polymer material including a polymer, a filler, and a modifying agent, in which the affinity to the filler, of the polymer to which the modifying agent is added, can be evaluated in a short period of time.

According to the present invention, a computer-implemented method for simulating a polymer material including a polymer, a filler, and a modifying agent for increasing the affinity of the polymer to the filler, comprising:

a process in which a virtual space is defined so that the virtual space has a pair of parallelly-opposed wall surfaces;

a process in which a plurality of modified polymer models are defined in the virtual space,
wherein each of the modified polymer models includes a polymer model of the polymer, comprising at least one particle, and a modifying agent model of the modifying agent, comprising at least one particle representing a modifying group of the modifying agent;

a process in which,
between the particles of the polymer models,
between the particles of the modifying agent models and
between the particles of the polymer models and the particles of the modifying agent models,
a repulsive potential which exerts a repulsive force between the particles concerned when the distance therebetween becomes less than a predetermined threshold, is defined;

a process in which a pair of filler models are defined by the parallelly-opposed wall surfaces of the virtual space;

an interactive potential defining process in which, between the filler models and the particles of the polymer models and between the filler models and the particles of the modifying agent models,
an interactive potential is defined which
exerts an attractive force or a repulsive force between the filler model and particle concerned when the distance therebetween is less than a predetermined threshold, and exerts no force between the filler model and particle concerned when the distance therebetween becomes more than the predetermined threshold, wherein
the threshold for the interactive potential defined between the filler model and the particle of the modifying agent model is more than the threshold for the interactive potential defined between the filler model and the particle of the polymer model, and
the intensity of the interactive potential defined between the filler model and the particle of the modifying agent model is higher than the intensity of the interactive potential defined between the filler model and the particle of the polymer model, a simulation process in which the filler models and the modified polymer models in the virtual space are relaxed by making molecular dynamics calculations, and an evaluation process in which, by the use of results obtained in the simulation process, the affinity of the particle of the modifying agent model to the filler model is evaluated, wherein the simulation process includes a process in which the number of the particles of the modifying agent models staying in a nearby-filler area is counted at constant time steps to acquire time-series counted numbers, wherein the nearby-filler area is a part of the virtual space extending from each of the filler models by a predetermined distance L1 perpendicularly thereto, and the evaluation process includes a process in which, using the time-series counted numbers, every two or more successive counted numbers are averaged and are output.

Preferably, the number of the successive counted numbers to be averaged in each time, is at least 5 and at most 1,000,000.

In the modified polymer model, the polymer model comprises a plurality of the particles, and between the particles of the polymer model, and between the particles of the polymer model and the particle or particles of the modifying agent model, a joining chain is defined by a coupling potential, wherein the coupling potential is defined between the particles concerned so that,
when the distance therebetween becomes increased over a distance which is determined by the intensity of the repulsive potential and the intensity of the coupling potential, the coupling potential dominantly exerts an attractive force whose magnitude is larger than the magnitude of the repulsive force resulting from the repulsive potential defined between the particles concerned, and further
the coupling potential is defined so as to exerts an attractive force whose magnitude is larger than the magnitude of an attractive force resulting from the interactive potential defined between the particle concerned and any of the filler models.

In this invention, therefore, the filler models are fixed to the virtual space. Under such condition, to be calculated is the dispersion or motions of the modified polymer models only. Accordingly, the relaxation calculation can be completed in a short period of time.

Further, the direction of the interactive potential field caused by the filler model is one direction perpendicular to the wall surface, in contrast to a spherical filler model resulting in radial directions or all directions. Therefore, the relaxation calculation becomes relatively simple and the computational time may be further reduced.

Furthermore, since every two or more successive counted numbers are averaged, it is possible to accurately evaluate the affinity to the filler, of a polymer material with a modifying agent.

DESCRIPTION OF THE PREFERRED EMBODIMENTS

Embodiments of the present invention will now be described in detail in conjunction with accompanying drawings.

The simulation method according to the present invention is to simulate a polymer material or mixture including a polymer, a filler and a modifying agent to increase the affinity of the polymer to the filler in order to evaluate the effect of the modifying agent and to estimate the characteristics of the cured polymer material.

Here, the filler may be any kind of filler including carbon black, silica, alumina and the like.

The polymer may be any kind of polymer including rubber, elastomer, resin and the like.

The modifying agent may be any kind of modifying agent having a functional group which is an atom group including a hydroxyl group or carbonyl group.

Figure 1:
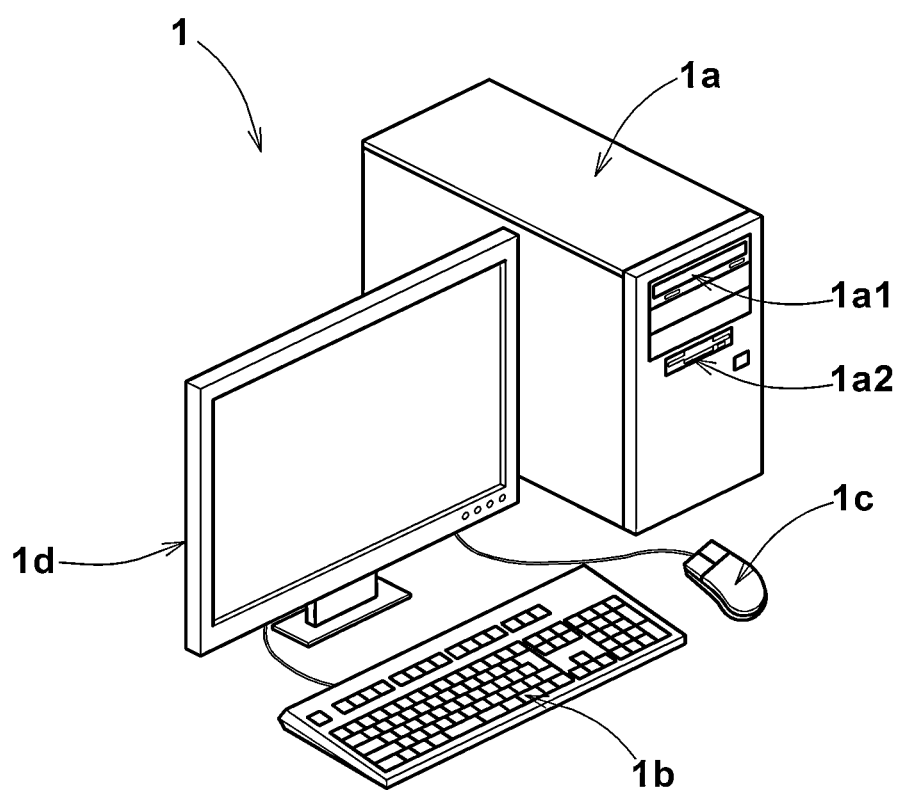
FIG. 1 is a perspective view of a computer system for implementing a simulation method as an embodiment of the present invention.

As shown in FIG. 1 for example, the computer system 1 implementing the simulation method comprises a main body 1a, a keyboard 1b, a mouse 1c and a display 1d. The main body 1a comprises an arithmetic processing unit (CPU), memory, storage devices such as magnetic disk, disk drives 1a1 and 1a2 and the like. In the storage device, programs/software for carrying out the simulating method are stored.

Figure 2:
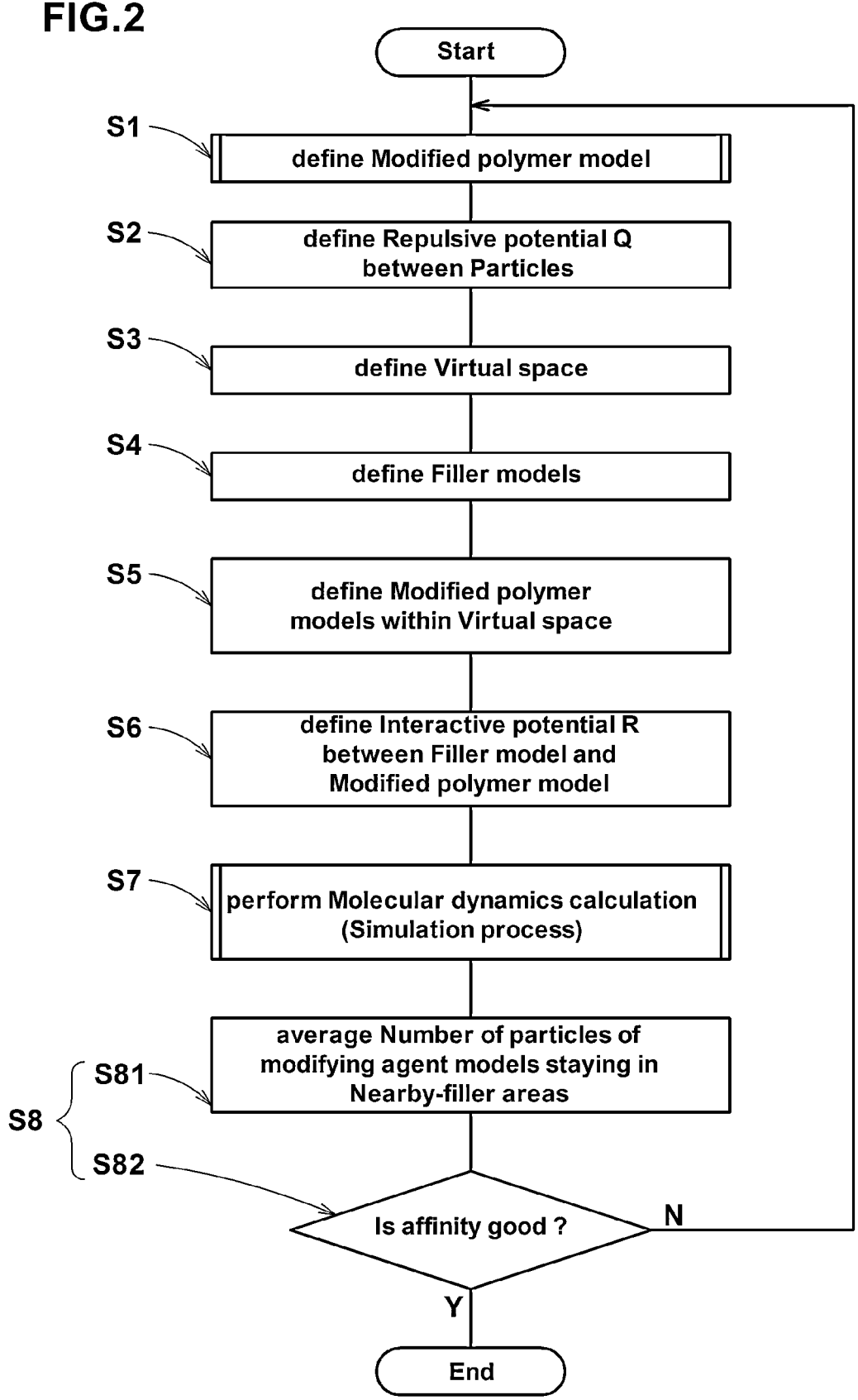
FIG. 2 is a flow chart of the simulation method.

FIG. 2 shows a flowchart of the simulation method as an embodiment of the present invention. This flowchart is just for illustrative purposes. It is not always necessary to perform these processes in this order.

*Process S1

Figure 3:
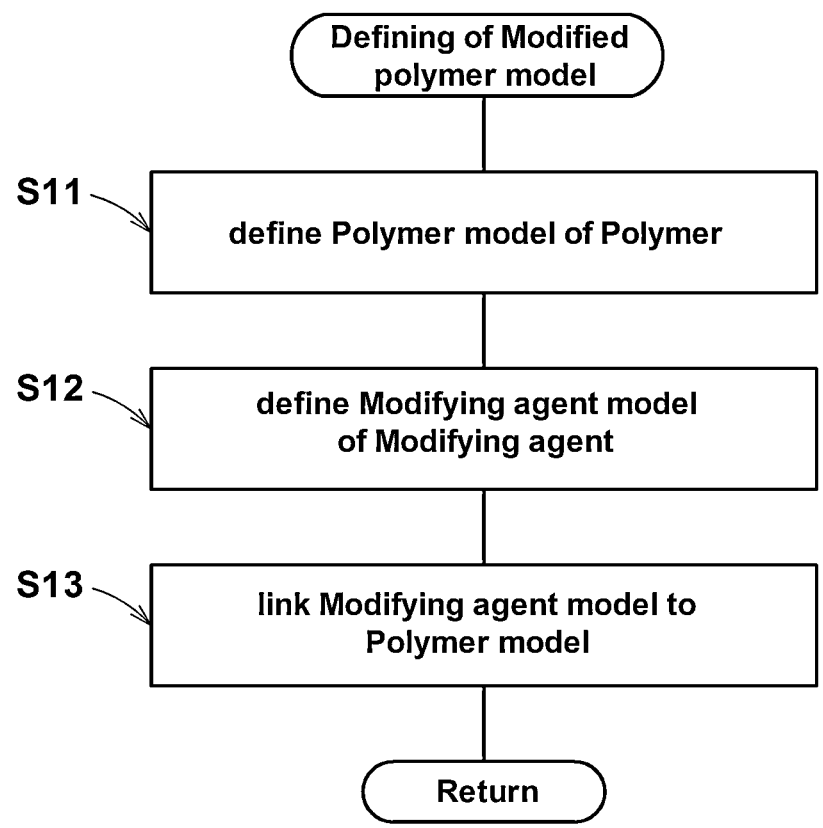
FIG. 3 is a flow chart of the process for defining the modified polymer model.

In the process S1, a modified polymer model 2 made up of a polymer model 3 and a modifying agent model 7 is defined,
FIG. 3 shows a flowchart of this process S1.

**Process S11

In this process S11, a polymer model 3 of the polymer is defined.

Figure 4:
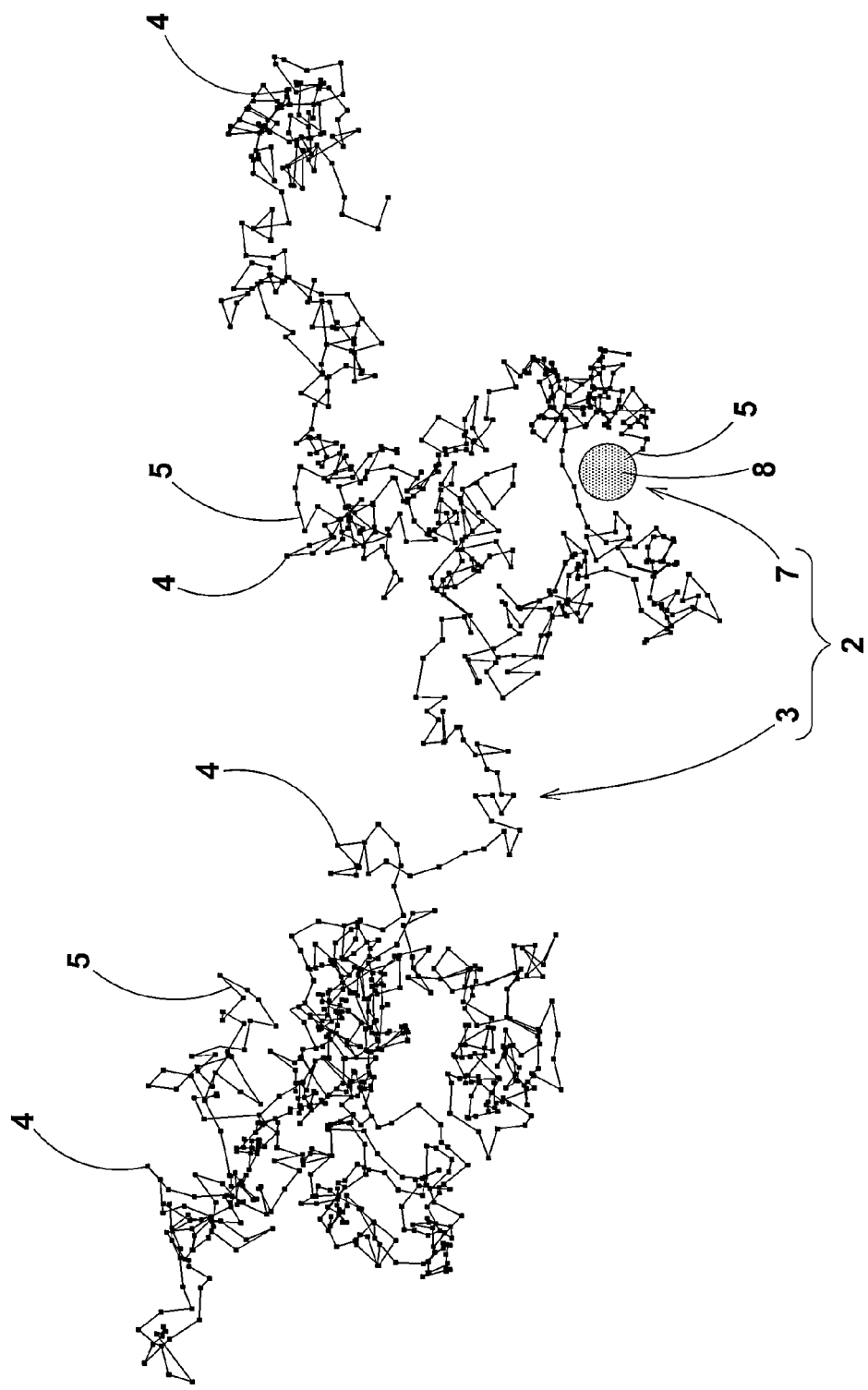
FIG. 4 shows an example of the modified polymer model.

As shown in FIG. 4, the polymer model 3 comprises at least one, in this example, a plurality of particles 4 defined according to a coarse-grained molecular dynamic method so that each particle 4 represents a plurality of monomers.

The polymer model 3 is, of course, a set of numerical data (inclusive of data on the mass, volume, diameter and initial stage coordinates of each particle 4) to be used in a molecular dynamics calculation, and the numerical data are stored in the computer 1.

Figure 5:
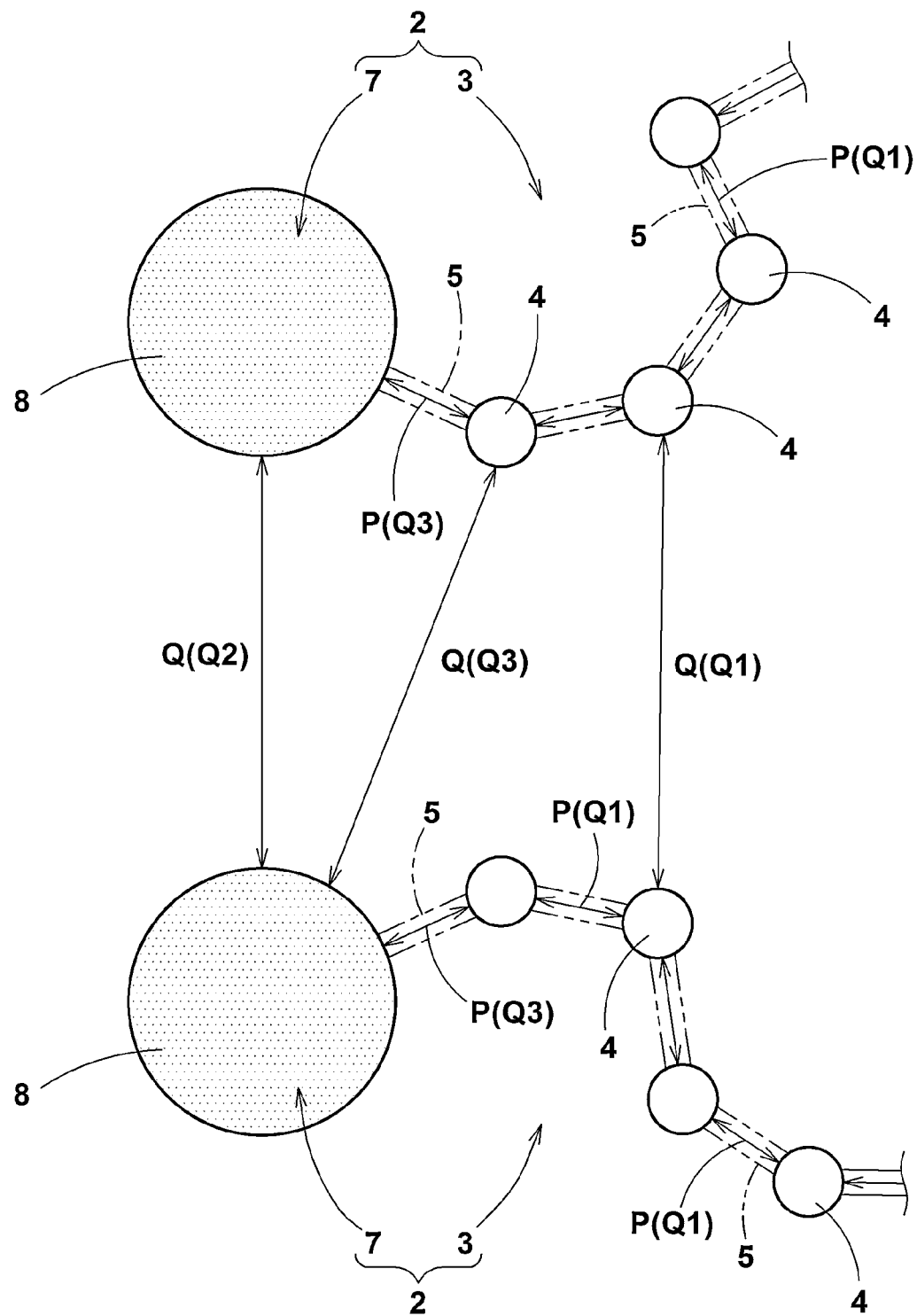
FIG. 5 shows two adjacent modified polymer models.

In this example, one polymer model 3 includes a plurality of the particles 4, and
a joining chain 5 is defined between the particles 4 as shown in FIG. 5 so that the distance therebetween is variable to a limited extent. For example, the number of the particles 4 is 1000. The polymer model 3 represents a three-dimensional straight-chain structure of the polymer.

As the joining chain 5, a coupling potential P given by the following equation (1) is defined.

$$P = \begin{cases} -0.5kR_0^2 \ln\left[1 - \left(\frac{r_{ij}}{R_0}\right)^2\right] & \text{if } r_{ij} < R_0 \\ \infty & \text{if } r_{ij} \geq R_0 \end{cases} \quad (1)$$

wherein
k: a coefficient for the intensity of the coupling potential P between the particles 4 concerned,
$r_{ij}$: the distance between the centers of the particles 4 concerned, and
$R_0$: a predetermined allowable maximum distance between the centers of the particles 4 concerned.

In the equation (1), therefore, when the distance $r_{ij}$ is less than the allowable maximum distance $R_0$, the coupling potential P restricts the relative motion of the particles 4 according to the distance $r_{ij}$ between the particles 4 so that the distance $r_{ij}$ does not increase over the allowable maximum distance $R_0$ and may be restored to the original.

If however, the value of the distance $r_{ij}$ becomes increased over the allowable maximum distance R0, then infinity is set to the coupling potential P so that the distance $r_{ij}$ does not increase over the allowable maximum distance $R_0$.
Thus, the joining chain 5 is defined to have an elongation limit.

As to the coefficient k for the intensity of the coupling potential P and the allowable maximum distance $R_0$, any suitable values may be set thereto. In this embodiment, "30" is set to the coefficient k, and
"1.5" is set to the allowable maximum distance $R_0$ according to Non-patent document ("Dynamics of entangled linear polymer melts; A molecular-dynamics simulation" Journal of Chemical Physics, Volume 92, Issue 8, 15 Apr. 1990)

**Process S12

In the process S12, a modifying agent model 7 of the modifying agent is defined.

The modifying agent model 7 comprises at least one particle 8, in this example as shown in FIG. 4 and FIG. 5, only one particle 8, representing a modifying group or a functional group of the modifying agent.

Similarly, the modifying agent model 7 is a set of numerical data (inclusive of data on the mass, volume, diameter and initial stage coordinates of particle 8) to be used in the molecular dynamics calculation. The numerical data are stored in the computer 1.

**Process S13

In the process S13, the modifying agent model 7 is linked to the polymer model 3, and a modified polymer model 2, which is made up of the polymer model 3 and the modifying agent model 7, is defined, wherein
in order to link between the particle 8 of the modifying agent model 7 and one of the particles 4 of the polymer model 3, a joining chain 5 as described above is defined by the above-mentioned coupling potential P given by the equation (1).

*Process S2

In the process S2, as shown in FIG. 5, between the particles 4 and 4 of the polymer model 3, and between the particles 8 and 8 of the modifying agent model 7 (if plural particles 8 exist), and further
between the particle 4 and particle 8,
a repulsive potential Q given by the following equation (2), is defined.

$$Q = \begin{cases} 4\varepsilon\left[\left(\frac{\sigma}{r_{ij}}\right)^{12} - \left(\frac{\sigma}{r_{ij}}\right)^{6} + \frac{1}{4}\right] & \text{if } r_{ij} < 2^{\frac{1}{6}}\sigma \\ 0 & \text{if } r_{ij} \geq 2^{\frac{1}{6}}\sigma \end{cases} \quad (2)$$

wherein
$\varepsilon$: a coefficient for the intensity of the repulsive potential Q between the particles concerned,
$r_{ij}$: the distance between the centers of the particles concerned,
$\sigma$: a coefficient for adjusting the threshold of the distance $r_{ij}$ or the effective Lennard-Jones particle diameter.

In the equation (2), when the distance $r_{ij}$ is less than the predetermined threshold $2^{1/6}\sigma$, the repulsive potential Q is increased with the decrease in the distance $r_{ij}$, and the repulsive potential Q becomes equal to the above-mentioned coupling potential P. Thereby, the distance between the particles 4 and 4 between which the joining chain 5 is defined, and the distance between the particle 4 and particle 8 between which the joining chain 5 is defined are stably-maintained, and the modified polymer model 2 can maintain its three-dimensional straight-chain structure.

If however, the value of the distance $r_{ij}$ becomes longer than the threshold $2^{1/6}\sigma$, then zero is set to the repulsive potential Q so that the repulsive force becomes zero.

The repulsive potential Q is also defined between the modified polymer models 2 and 2.

In the example shown in FIG. 5, the following repulsive potentials Q1 to Q3 are defined.
Q1: between particle 4 and particle 4 in each modified polymer model 2,
Q1: between particle 4 in a modified polymer model 2 and particle 4 in another modified polymer model 2,
Q2: between particle 8 in a modified polymer model 2 and particle 8 in another modified polymer model 2,
Q3: between particle 4 and particle 8 in each modified polymer model 2,
Q3: between particle 4 in a modified polymer model 2 and particle 8 in another modified polymer model 2.

Any suitable values may be set to the coefficient e of each of the repulsive potentials Q1 to Q3.

In this embodiment, "1.0" is set to each, according to the above-mentioned Non-patent document so that the repulsive potentials Q1 to Q3 may have an identical intensity.

*Process S3

In the process S3, there is defined a virtual space 6 having a predetermined volume and a pair of parallelly-opposed wall surfaces 11 and 11 between which the modified polymer model 2 is disposed.

In this example, the shape of the virtual space 6 is a regular hexahedron having three pairs of parallelly-opposed wall surfaces 11. There is defined a condition such that the modified polymer model 2 can not pass through the wall surface 11.

*Process S4

Figure 6:
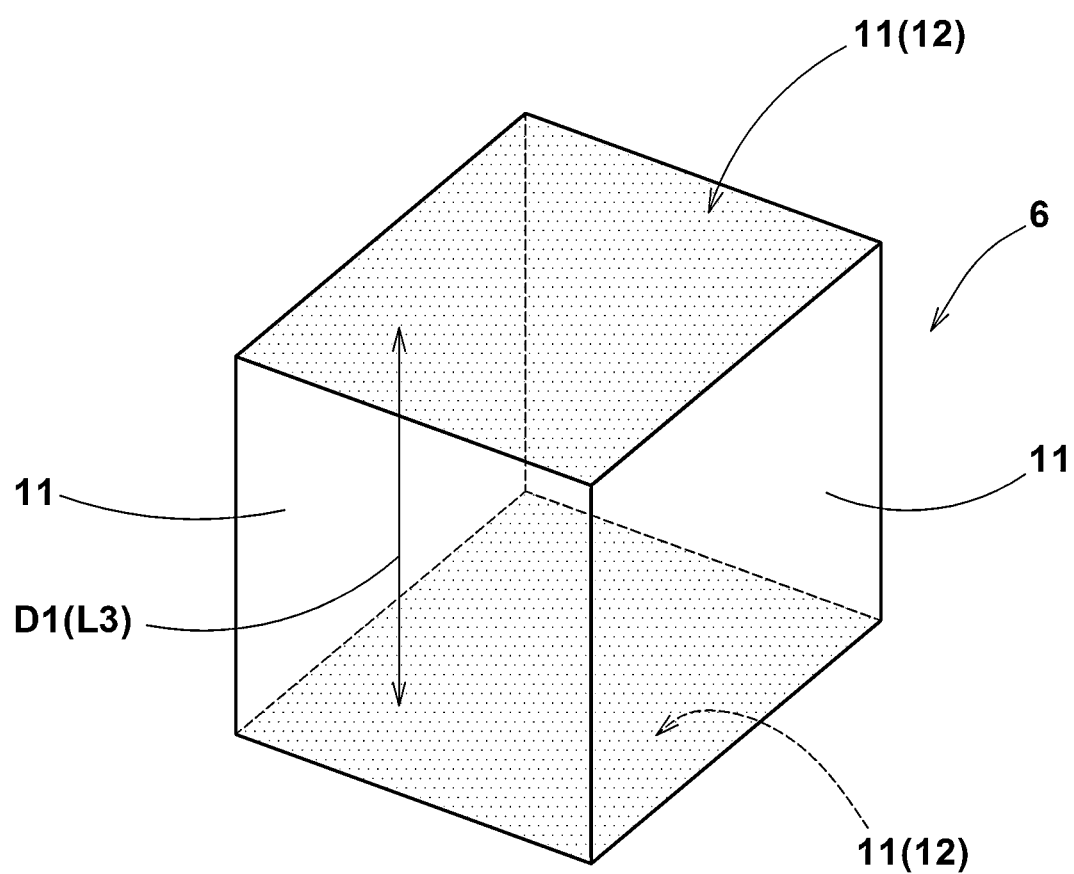
FIG. 6 is a perspective view of an example of the virtual space.

In the process S4, a pair of filler models 12 and 12 are respectively defined by a pair of the above-mentioned parallelly-opposed wall surfaces 11 and 11. Namely, according to the present invention, each filler model 12 is defined by a flat face instead of a particle (or spherical surface). In the example shown in FIG. 6, the wall surfaces 11 and 11 which are parallelly-opposed in the up-and-down direction are used as filler models 12 and 12, respectively.

The paired filler models 12 are accordingly immovable with respect to the virtual space 6.

*Process S6

Figure 8:
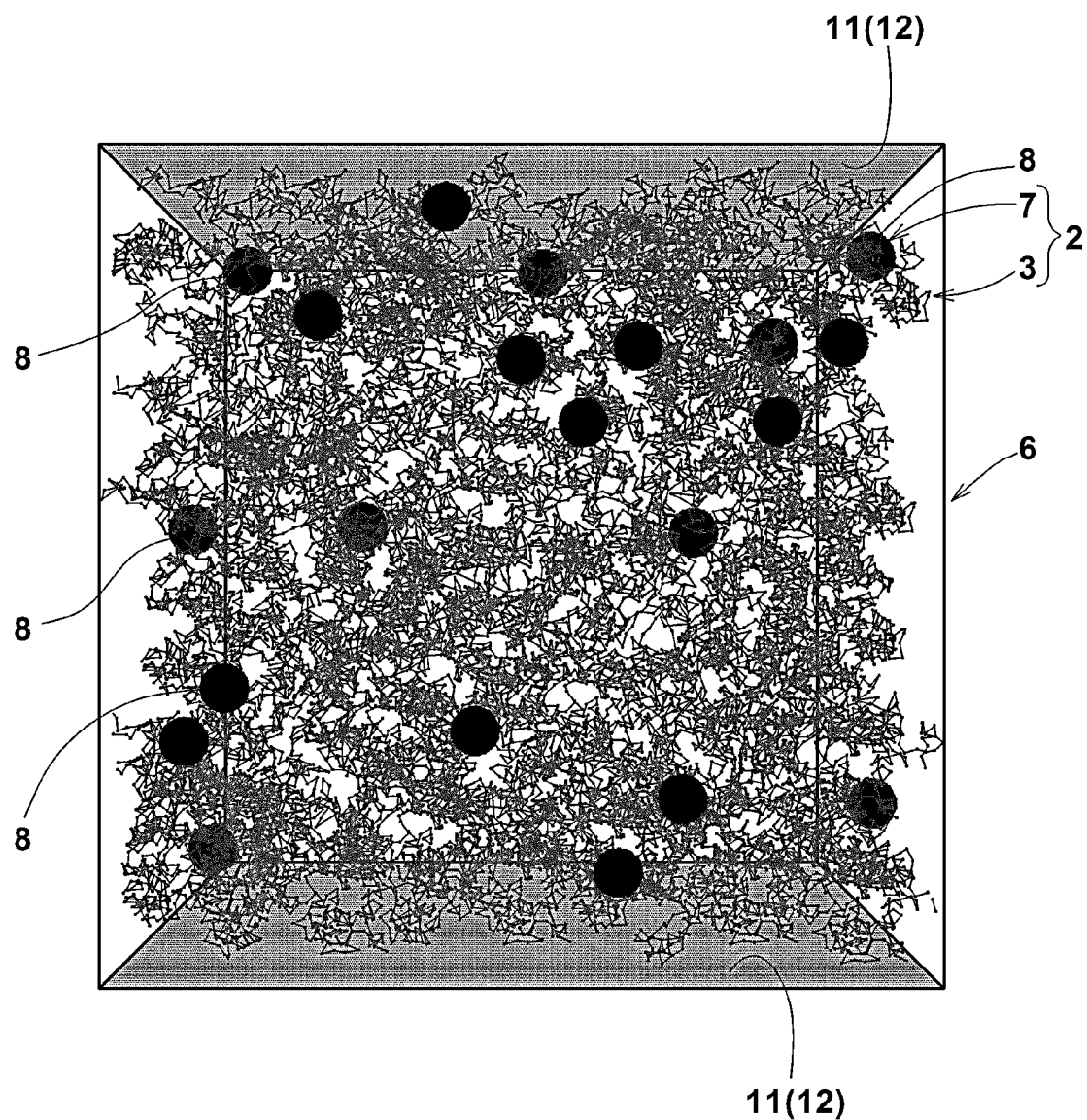
FIG. 8 shows an initial state of the modified polymer models disposed in the virtual space

In the process S6, as shown in FIG. 8, a plurality of the modified polymer models 2 are arranged or defined within the virtual space 6 namely between the paired filler models 12 and 12. Initially, they are arranged randomly. In the example shown in FIG. 8, each black circle represents one particle 8. The number of the modified polymer models 2 arranged in the virtual space 6 is about twenty to forty for example.

It is desirable that the distance D1 (length L3 of a side) between the paired parallelly-opposed wall surfaces 11 measured perpendicularly thereto is not less than 2 times, preferably not less than 4 times the radius of inertia of the modified polymer model 2. Thereby, in the after-mentioned molecular dynamics calculation, it becomes possible to stably calculate the rotational motion of the modified polymer model 2 in the virtual space 6.

*Process S5

In the process S5, between the filler model 12 and the modified polymer model 2, an interactive potential R which can exert an attractive force or a repulsive force therebetween according to their distance, is defined.

Figure 7:
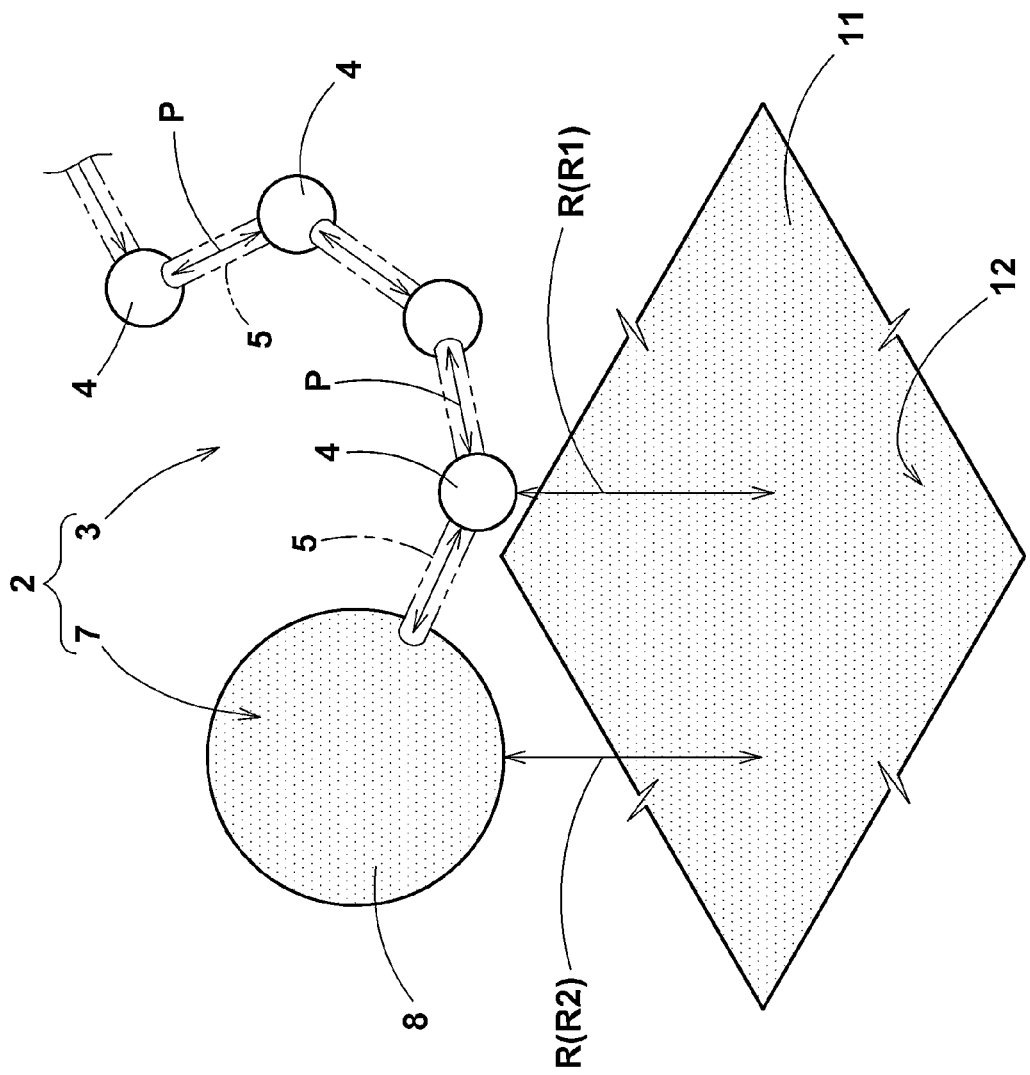
FIG. 7 is a diagram for explaining the interactive potentials defined between the filler model and the modified polymer model.

In the example shown in FIG. 7,
between the filler model 12 and the particle 4 (simulating a nonmodified group), and
between the filler model 12 and the particle 8 (simulating a modified group),
the interactive potential R given by the following equation (3) is defined.

$$R = \begin{cases} 4\pi\rho_{wall}\varepsilon_{wall}\left[\frac{1}{5}\left(\frac{\sigma_{wall}}{r}\right)^{10} - \frac{1}{2}\left(\frac{\sigma_{wall}}{r}\right)^{4}\right] & \text{if } r < r_c \\ 0 & \text{if } r \geq r_c \end{cases} \quad (3)$$

wherein
r: the distance between the filler model and the center of the particle 4 or 8 concerned,
$r_c$: a threshold of the distance,
$\rho_{wall}$: a coefficient relating to the areal density of the interactive potential R,
$\varepsilon_{wall}$: a coefficient relating to the intensity of the interactive potential R, $\sigma_{wall}$: a coefficient relating to the distance from the filler model (wall surface 11).

The equation (3) can be obtained by integrating the repulsive potential Q defined by the equation (2) over the wall surface 11 (the filler model 12).

In the equation (3), if the distance r becomes more than the predetermined threshold rc, the interactive potential R does not exert.

If the distance r is less than $\sigma_{wall} \times 2^{1/6}$, the interactive potential R exerts a repulsive force between the filler model 12 and the particle 4, 8.

If the distance r is more than $\sigma_{wall} \times 2^{1/6}$, the interactive potential R exerts an attractive force between the filler model 12 and the particle 4, 8.

Thus, the equation (3) defines an attractive force or repulsive force between the filler model 12 and the particle 4, 8 according to the distance r therebetween.

In the example shown in FIG. 7, the following interactive potentials R1 and R2 are defined.
R1: between filler model 12 and particle 4 (nonmodified)
R2: between filler model 12 and particle 8 (modified)

Any suitable values may be set to $\rho_{wall}$, $\sigma_{wall}$, $\epsilon_{wall}$ and $r_c$ of the interactive potentials R1 and R2.

In this embodiment, these parameters are set as follows.
interactive potential R1:
  $\rho_{wall}=1.0$
  $\sigma_{wall}=1.0$
  $\epsilon_{wall}=1.0$
  $r_c=1.12$
interactive potential R2:
  $\rho_{wall}=1.0$
  $\sigma_{wall}=1.0$
  $\epsilon_{wall}=5.0$
  $r_c=2.5$ By setting the value of $\epsilon_{wall}$ (=5) of the interactive potential R2 larger than the value of $\epsilon_{wall}$ (=1) of the interactive potential R1 as above, the intensity of the attractive force or repulsive force between the filler model 12 and the particle 8 can increase more than that between the filler model 12 and the particle 4.

By setting 2.5 to the threshold $r_c$ for the interactive potential R2, in a relatively wide range of the distance r from $2^{1/6}$(=1.12) to 2.5, the interactive potential R2 can exert an attractive force between the filler model 12 and the particle 8. By setting 1.12 to the threshold $r_c$ for the interactive potential R1, the interactive potential R2 exerts only a repulsive force between the filler model 12 and the particle 4. Accordingly, the particle 8 (modified) receives an attractive force dominantly than the particle 4 (nonmodified).

Thus, by setting the $\epsilon_{wall}$ and $r_c$ of the interactive potentials R1 and R2 as explained above, the affinity of the particle 8 to the filler model 12 can be defined as being higher than the affinity of the particle 4 to the filler model 12.

*Simulation Process S7

In the simulation process S7, a relaxation of the particles 4 and 8 of the modified polymer models 2 between the filler models 12 is simulated by performing molecular dynamics calculations.

In this example, on the assumption that the particles 4 and 8 of the modified polymer models 2 accords with classical dynamics, Newton's equation of motion is applied to the molecular dynamics calculation. And the motion of the particles 4 and 8 are tracked at constant time interval.

During the calculation, the number of the particles in the virtual space 6, and the temperature and the volume of the virtual space 6 are kept constant.

Since the filler model 12 is locked to a pair of the parallelly-opposed wall surfaces 11 of the virtual space 6, the relaxation calculation can be performed, targeting at the modified polymer model 2 only. Therefore, the computational time is remarkable reduced when compared with a relaxation calculation performed targeting at both of the modified polymer models and movable filler models.

Further, the direction of the interactive potential field caused by the filler model 12 is one direction perpendicular to the wall surface 11, in contrast to a spherical filler model resulting in radial directions or all directions. Therefore, the relaxation calculation becomes relatively simple and the computational time may be further reduced.

Figure 10:
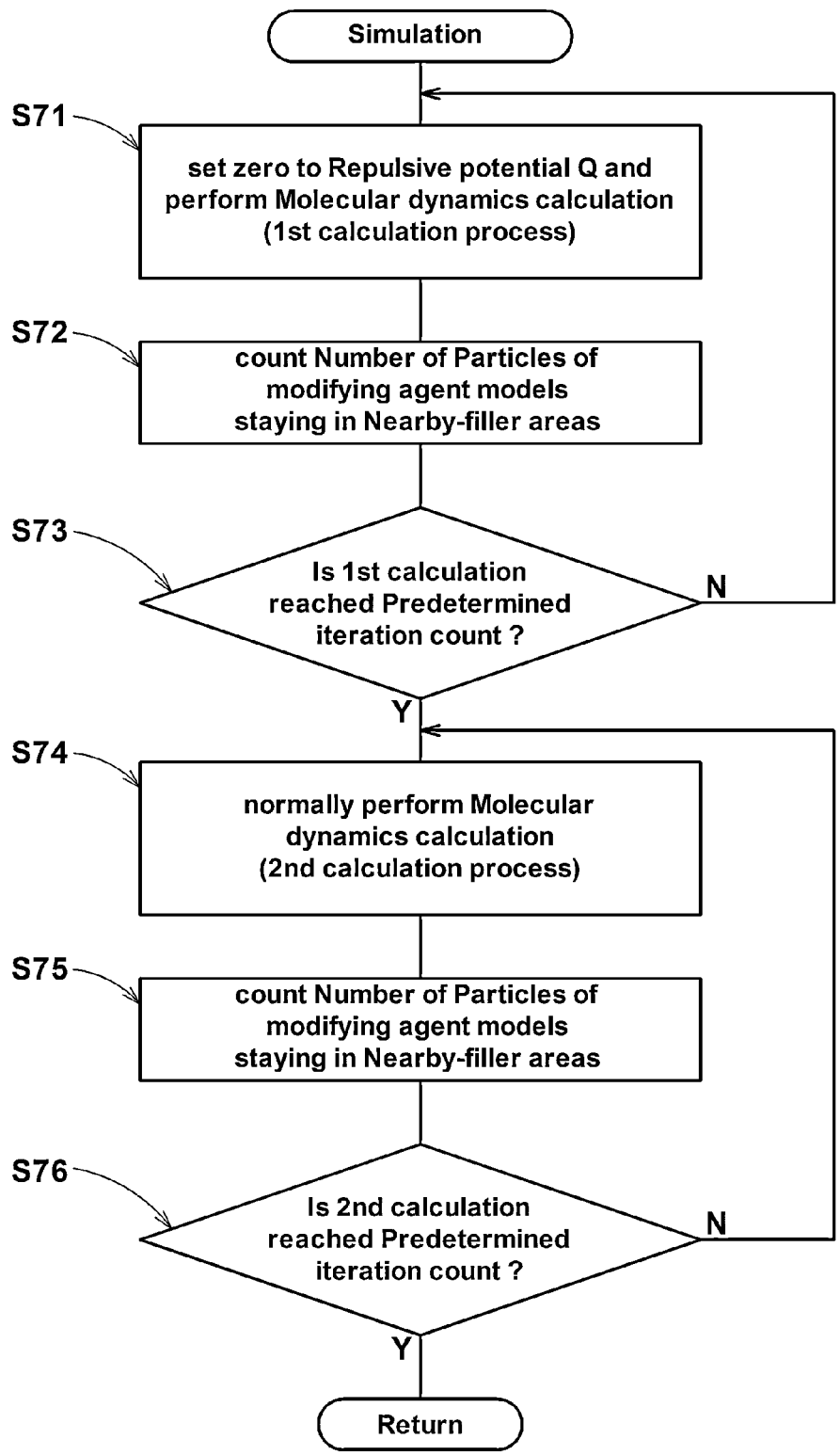
FIG. 10 is a flow chart of the simulation process.

FIG. 10 shows a flowchart of a more specific example of the simulation process S7. As shown, this example includes a first calculation process S71 and a second calculation process S74 performed thereafter.

**Process S71

In the first calculation process S71, a molecular dynamics calculation is performed under such condition that only the repulsive potential Q is made ineffective, in other words, with respect to every possible combinations of the particles 4 and 8 of the modified polymer models 2, the repulsive potential Q (FIG. 5) is defined such that the resultant repulsive force is always zero, while the coupling potential P and the interactive potential R are maintained as defined as above.

For example, by setting zero to the coefficient $\epsilon$ of the equation (2) adjusting the intensity of the repulsive potential Q, the repulsive force is made zero.

In the first calculation process S71, therefore, by mandatorily setting zero to the repulsive force, it becomes possible, in the calculation, that the modified polymer models 2 in the virtual space 6 are moved without hindering each other. Therefore, it is possible that each modified polymer model 2 comes close to another modified polymer model 2. As a result, the relaxation of the modified polymer models 2 can be made in a short period of time

**Process S72

Figure 9:
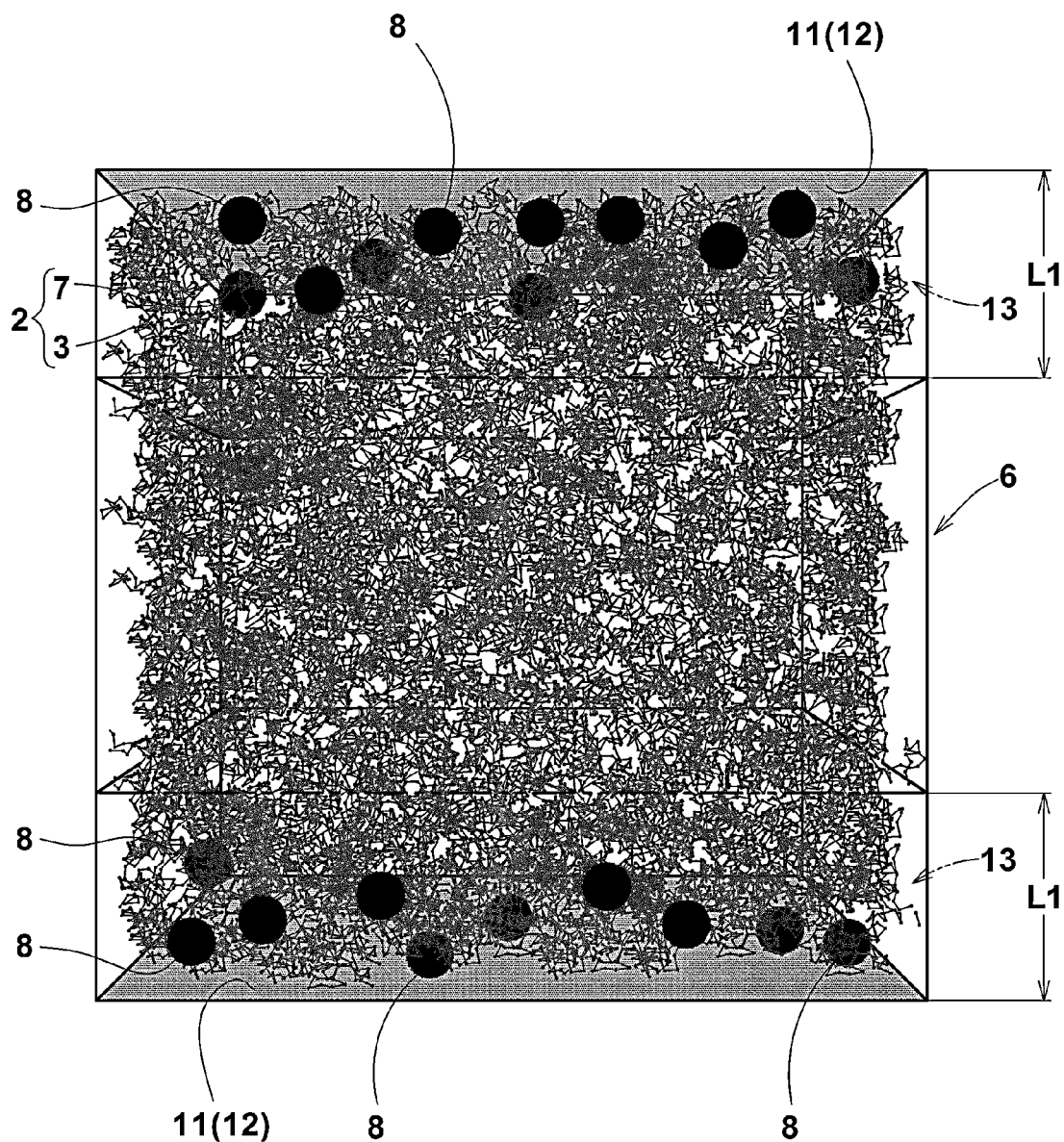
FIG. 9 shows a state of the modified polymer models in the virtual space after the relaxation calculation has been completed according to an embodiment of the present invention.

In the process S72, the number of the particles 8 staying in a nearby-filler area 13 is counted, and the counted number is acquired at constant time steps and stored in the computer 1. Here, the nearby-filler area 13 is a part of the virtual space 6 extending from each of the filler model 12 by a predetermined distance L1 perpendicularly to the filler model 12 as shown in FIG. 9.

The distance L1 is preferably set in a range of from $2^{1/6}$ (nearly equal 1.12) to 2.5 times the coefficient $\sigma_{wall}$ for the interactive potential R.

The particles 8 staying in the nearby-filler area 13 are considered as well approaching the filler model 12. Therefore, by counting the number of the particles 8, the affinity of the particle 8 to the filler model 12 can be evaluated.

If the distance L1 is less than $2^{1/6}$ times the coefficient $\sigma_{wall}$ for the interactive potential R, only a repulsive force occurs between the particle 8 in the nearby-filler area 13 and the filler model 12. Accordingly, even if the particle 8 is once moved into the nearby-filler area 13, the particle 8 soon moves out of the nearby-filler area 13. Therefore, it is difficult to estimate the affinity.

On the other hand, the distance L1 set to be more then 2.5 times the coefficient $\sigma_{wall}$ increases the particles 8 whose distance r exceeds the threshold rc(=2.5) and accordingly the interactive potential R2 (exerting an attractive force) between the particle 8 and the filler model 12 becomes void. Therefore, the number of the particles 8 approaching the filler model 12 tends to increase and it becomes difficult to estimate the affinity. In this example, the distance L1 is 2 times the coefficient $\sigma_{wall}$.

Figure 11A:
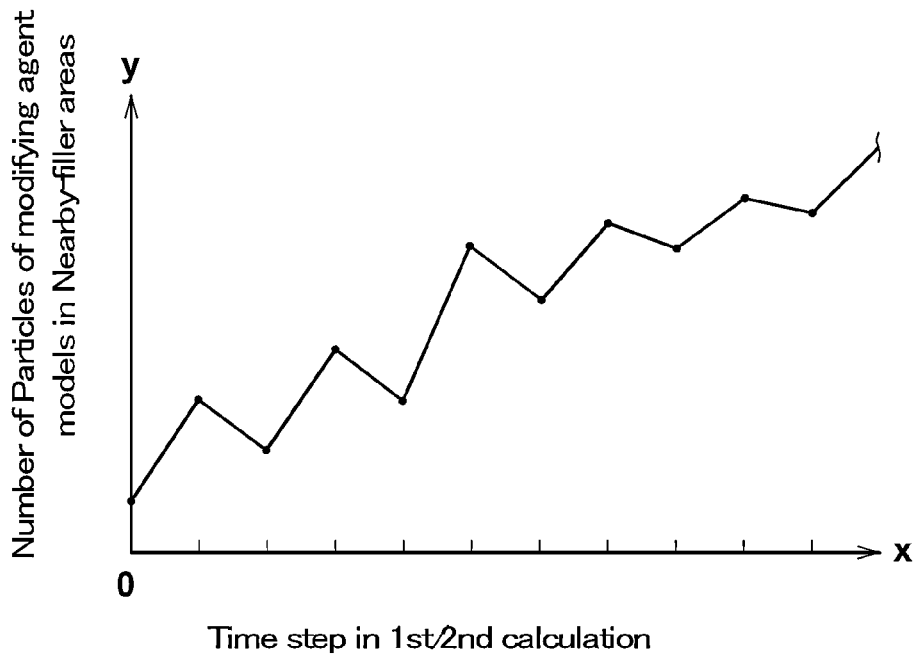
FIG. 11(a) is a graph showing the variation of the number of the particles of the modifying agent models staying in the nearby-filler area with the progress of time (time steps).

FIG. 11(a) shows an example of the variation of the counted number of the particles 8 of the modifying agent models 7 staying in the nearby-filler area 13 with the progress of time (the increase in the time steps).

During the molecular dynamics calculation, there are the particles 8 moving into the nearby-filler area 13 and the particles 8 moving out of the nearby-filler area 13 owing to the attractive force and repulsive force. As a result, the variation of the counted number usually becomes zigzag as shown in FIG. 11(a).

**Process 73

In the process 73, it is judged if the number of time steps, namely, the number of iterations of the first calculation process S71 has reached to a predetermined value.

If not, the processes S71 to S72 are repeated.

If yes, the second calculation process S74 is performed by the computer 1.

In order to effectively relax the modified polymer models 2, the molecular dynamics calculation in the first calculation process S71 is preferably iterated 1000 to 10,000,000 times (in this example, 1,000,000 times).

**Process S74

In the second calculation process S74, a molecular dynamics calculation is normally performed without mandatorily setting zero to the repulsive force resulted from the repulsive potential Q.

In this example, to make the repulsive potential Q effective, the original value (1.0) is set to the coefficient e to which zero is once set in the first calculation process S71.

Thus, through the first calculation process S71, the modified polymer models 2 are well dispersed in a short period of time.

Then, through the second calculation process S74, the molecular dynamics calculation is performed under the normal conditions. Therefore, it is possible to make an accurate relaxation in a short period of time.

**Process S75

In the process S75, the number of the particles 8 moved into the nearby-filler area 13 and staying therein is counted, and the counted number is acquired at constant time steps and stored in the computer 1 in the same manner as in the process S72.

**Process S76

In the process S76, it is judged if the number of time steps, namely, the number of iterations of the second calculation process S74 has reached to a predetermined value.

If not, the processes S74 to S75 are repeated.

If yes, the simulation process S7 is ended and the processing goes to the next process.

In order to minimize the error of the simulation results, the molecular dynamics calculation in the second calculation process S74 is preferably iterated 1000 to 1,000,000 times (in this example, 300,000 times).

*Evaluation Process S8

In the evaluation process S8, by the use of the results of the simulation process S7, the affinity of the particle 8 to the filler model 12 is evaluated. A more specific procedure is as follows.

*Process S81

First, using the time-series counted numbers of the particles 8 staying in the nearby-filler area 13 which has been acquired at constant time steps and stored in the memory or storage device in the process S74 and the process S75, the computer averages every two or more successive counted numbers (namely, every combinations of two or more successive counted numbers).

Figure 11B:
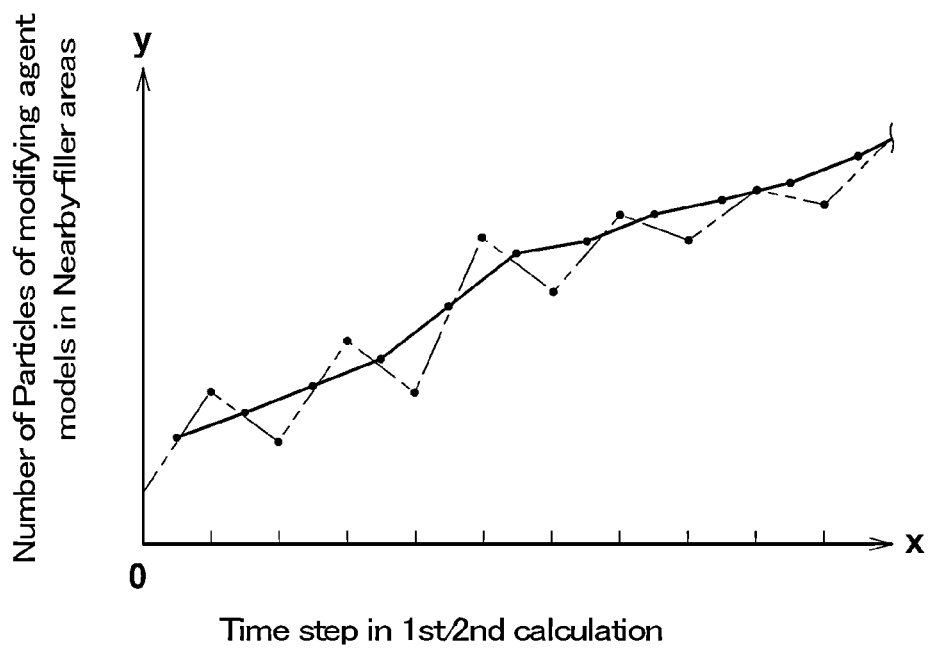
FIG. 11(b) is a graph showing the variation in FIG. 11(a) smoothened by averaging every two successive numbers.

In the example shown in FIG. 11(b), every two successive counted numbers are averaged.

The number of the successive counted numbers to be averaged in each time, is preferably at least 5, more preferably at least 20, but in view of balance between accuracy and computational cost, at most 1,000,000, preferably at most 10,000.

*Process S82

Next, it is judged whether the affinity of the modified polymer model 2 to the filler model 12 is good or not.

The criterion for judgment is such that the value of the average of the counted numbers corresponding to the ending time of the simulation process S7 (for example, the rightmost data in FIG. 11(a)) is within a range from a predetermined value Nmin % to 100% of the total number of the particles 8. The value Nmin is more than (the total volume of the nearby-filler areas 13/the volume of the virtual space 6)×100. In this example, the value Nmin is more than (L1×2/L3)×100, for example 2 times the value (L1×2/L3)×100.

If the affinity is judged as being good (within the above-mentioned criterion range), the simulation method ends.

If the affinity is judged as being not good (outside the criterion range), for example, the conditions defined on the modified polymer model 2 and/or filler model 12 are changed and then the processes S1 to S7 are performed.

Therefore, the simulation method can be used to find good conditions to disperse the modified polymer models 2 so that the modified polymer models 2 function effectively.

Although the invention has been described in accordance with the flowchart shown in FIG. 2 with a certain degree of particularity, this flowchart is just for purposes of illustration or for convenience sake and not to be construed to limit the scope of the invention. It is understood by those skilled in the art that the most important point is to define the modified polymer models 2, filler models 12, potentials P, Q and R and various conditions before starting the simulation process S7, therefore, the order from S1 to S6 is not essential. It is to be understood that some of these processes S1-S6 may be performed simultaneously by the computer, and some of these processes S1-S6 may be performed in reverse order.

The invention claimed is:

1. A computer-implemented method for simulating a polymer material including a polymer, a filler, and a modifying agent for increasing the affinity of the polymer to the filler, comprising:

a process in which a virtual space is defined so that the virtual space has a pair of parallelly-opposed wall surfaces;

a process in which a plurality of modified polymer models are defined in the virtual space, wherein each of the modified polymer models includes a polymer model of the polymer, comprising at least one particle, and a modifying agent model of the modifying agent, comprising at least one particle representing a modifying group of the modifying agent;

a process in which, between the particles of the polymer models, between the particles of the modifying agent models and between the particles of the polymer models and the particles of the modifying agent models, a repulsive potential which exerts a repulsive force between the particles of the polymer models and the particles of the modifying agent models when a distance therebetween becomes less than a first predetermined threshold, is defined;

a process in which a pair of filler models are defined by the parallelly-opposed wall surfaces of the virtual space;

an interactive potential defining process in which, between the pair of filler models and the particles of the polymer models and between the pair of filler models and the particles of the modifying agent models, an interactive potential is defined which exerts an attractive force or a repulsive force between each of the pair of filler models and the particles of the polymer models and between each of the pair of filler models and the particles of the modifying agent models when the distance therebetween is less than a second predetermined threshold, and exerts no force between each of the pair of filler models and the particles of the polymer models and between each of the pair of filler models and the particles of the modifying agent models when the distance therebetween becomes more than the second predetermined threshold, wherein the second threshold for the interactive potential defined between the filler model and the particle of the modifying agent model is more than the second threshold for the interactive potential defined between the filler model and the particle of the polymer model, and the intensity of the interactive potential defined between the filler model and the particle of the modifying agent model is higher than the intensity of the interactive potential defined between the filler model and the particle of the polymer model, a simulation process in which the filler models and the modified polymer models in the virtual space are relaxed by making molecular dynamics calculations, wherein the simulation process includes a process in which a number of the particles of the modifying agent models staying in a nearby-filler area is counted at constant time steps to acquire time-series counted numbers, wherein the nearby-filler area is a part of the virtual space extending from each of the filler models by a predetermined distance L1 perpendicularly to the filler model, and an evaluation process in which, by the use of results obtained in the simulation process, an affinity of the particle of the modifying agent model to the filler model is evaluated to improve the affinity, wherein the evaluation process includes a process in which, using the time-series counted numbers, every two or more successive counted numbers are averaged and are output.

2. The method for simulating polymer material according to claim 1, wherein the two or more successive counted numbers to be averaged in each time, is at least 5 and at most 1,000,000.

3. The method for simulating polymer material according to claim 1, wherein in each of the modified polymer models, the polymer model comprises a plurality of particles, and between the particles of the polymer model, and between the particles of the polymer model and the particle or particles of the modifying agent model, a joining chain is defined by a coupling potential, wherein the coupling potential is defined between the particles of the polymer models and the particles of the modifying agent models so that, when a distance therebetween becomes increased over a distance which is determined by the intensity of the repulsive potential and the intensity of the coupling potential, the coupling potential dominantly exerts an attractive force whose magnitude is larger than the magnitude of the repulsive force resulting from the repulsive potential defined between the particles of the polymer models and the particles of the modifying agent models, and further the coupling potential is defined so as to exerts an attractive force whose magnitude is larger than the magnitude of an attractive force resulting from the interactive potential defined between the particle of the polymer models and the particles of the modifying agent models and any of the filler models.

4. The method for simulating polymer material according to claim 2, wherein in each of the modified polymer models, the polymer model comprises a plurality of particles, and between the particles of the polymer model, and between the particles of the polymer model and the particle or particles of the modifying agent model, a joining chain is defined by a coupling potential, wherein the coupling potential is defined between the particles of the polymer models and the particles of the modifying agent models so that, when a distance therebetween becomes increased over a distance which is determined by the intensity of the repulsive potential and the intensity of the coupling potential, the coupling potential dominantly exerts an attractive force whose magnitude is larger than the magnitude of the repulsive force resulting from the repulsive potential defined between the particles of the polymer models and the particles of the modifying agent models, and further the coupling potential is defined so as to exerts an attractive force whose magnitude is larger than the magnitude of an attractive force resulting from the interactive potential defined between the particle of the polymer models and the particles of the modifying agent models and any of the filler models.

* * * * *